(12) United States Patent
Avellanet

(10) Patent No.: US 6,352,539 B1
(45) Date of Patent: Mar. 5, 2002

(54) SURGICAL INSTRUMENT WITH ROTATABLE SHAFT

(75) Inventor: Francisco J. Avellanet, Coral Gables, FL (US)

(73) Assignee: Scilogy Corp., Miami, FL (US)

( * ) Notice: Subject to any disclaimer, the term of this patent is extended or adjusted under 35 U.S.C. 154(b) by 0 days.

(21) Appl. No.: 09/237,420

(22) Filed: Jan. 26, 1999

Related U.S. Application Data

(63) Continuation-in-part of application No. 09/143,751, filed on Aug. 31, 1998, and a continuation-in-part of application No. 09/143,984, filed on Aug. 31, 1998, which is a continuation-in-part of application No. 09/087,476, filed on May 29, 1998, and a continuation-in-part of application No. 09/060,969, filed on Apr. 15, 1998, and a continuation-in-part of application No. 09/044,203, filed on Mar. 17, 1998, and a continuation-in-part of application No. 08/843,405, filed on May 2, 1997, and a continuation-in-part of application No. 08/963,686, filed on Nov. 4, 1997, and a continuation-in-part of application No. PCT/US97/18057, filed on Oct. 7, 1997.

(51) Int. Cl.[7] ............................................. A61B 17/22
(52) U.S. Cl. ..................................... 606/113; 606/110
(58) Field of Search ............................. 605/110, 113, 605/114, 47

(56) References Cited

U.S. PATENT DOCUMENTS

| | | | | |
|---|---|---|---|---|
| 3,828,790 A | * | 8/1974 | Curtiss et al. ............... | 606/113 |
| 3,942,309 A | | 3/1976 | Cahill .............................. | 57/9 |
| 3,955,578 A | * | 5/1976 | Chamness et al. ............. | 606/47 |
| 4,294,254 A | | 10/1981 | Chamness .............. | 128/303.14 |
| 5,066,295 A | | 11/1991 | Kozak et al. ................... | 606/47 |
| 5,084,054 A | * | 1/1992 | Bencini et al. ............. | 606/113 |
| 5,788,710 A | | 8/1998 | Bates et al. .................. | 606/127 |
| 5,814,052 A | * | 9/1998 | Nakao et al. ................ | 606/115 |
| 5,984,920 A | * | 11/1999 | Steinbach ..................... | 606/47 |
| 6,027,460 A | * | 11/1999 | Shturman .................... | 600/585 |

FOREIGN PATENT DOCUMENTS

| | | | | |
|---|---|---|---|---|
| GB | 197692 | | 5/1923 | |
| WO | WO 92/22254 | * | 12/1992 | ................. 606/114 |

* cited by examiner

Primary Examiner—Jeffrey A. Smith
Assistant Examiner—Michael B. Priddy
(74) Attorney, Agent, or Firm—Solomon Zaromb; Patrick J. Walsh

(57) ABSTRACT

A surgical snare instrument includes an elongated tubular sheath having proximal and distal ends, a flexible torqueable shaft having proximal and distal ends extending through and axially movable relative to the sheath, a snare loop at the distal end of the shaft, and a handle coupled to the proximal ends of the sheath and shaft for moving the shaft relative to the sheath and for rotating the shaft relative to the sheath so that the snare loop, when extended beyond the distal end of the sheath, is rotatable relative to the distal end of the sheath. The shaft is preferably a multifilament twisted and drawn cable. The filaments of the multifilament twisted and drawn cable are preferably either stainless steel, nickel-titanium alloy, or a combination of the two. Such a shaft has been demonstrated to provide the high torqueability necessary for controlled rotation of the snare loop.

36 Claims, 4 Drawing Sheets

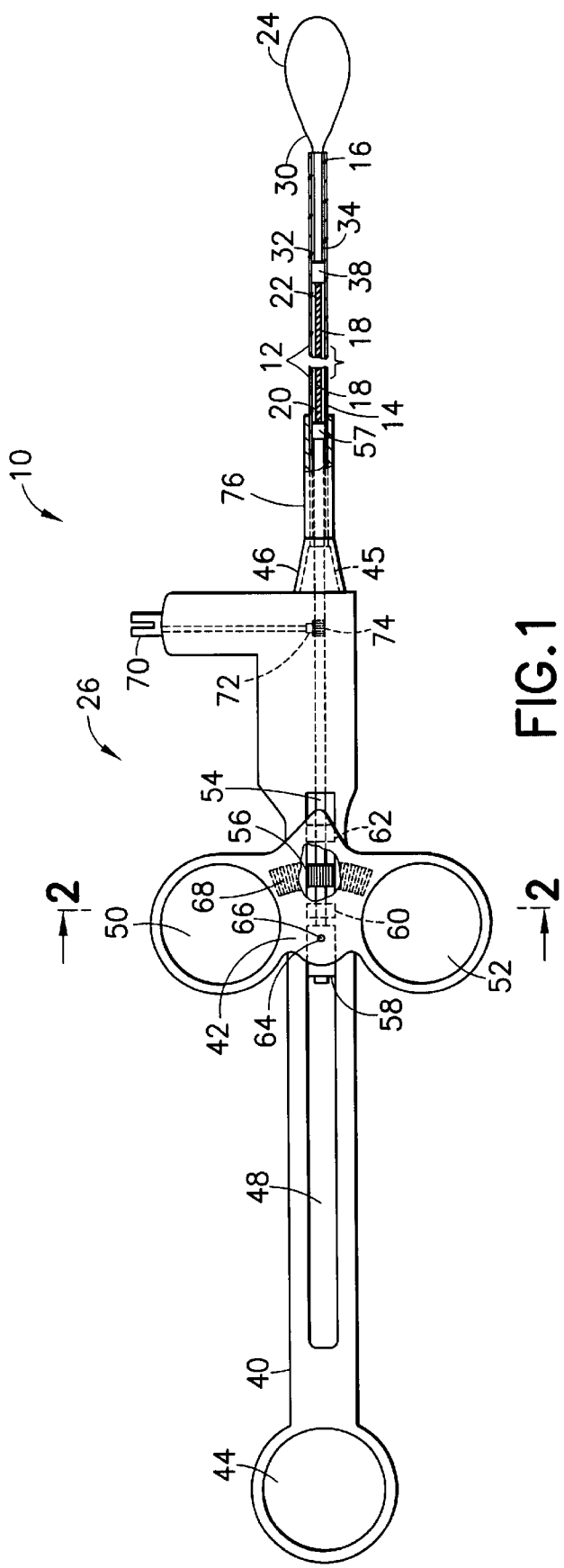
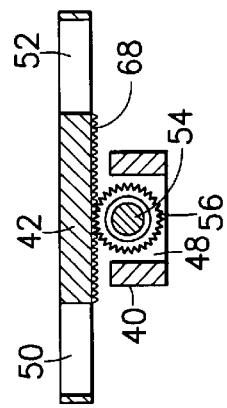

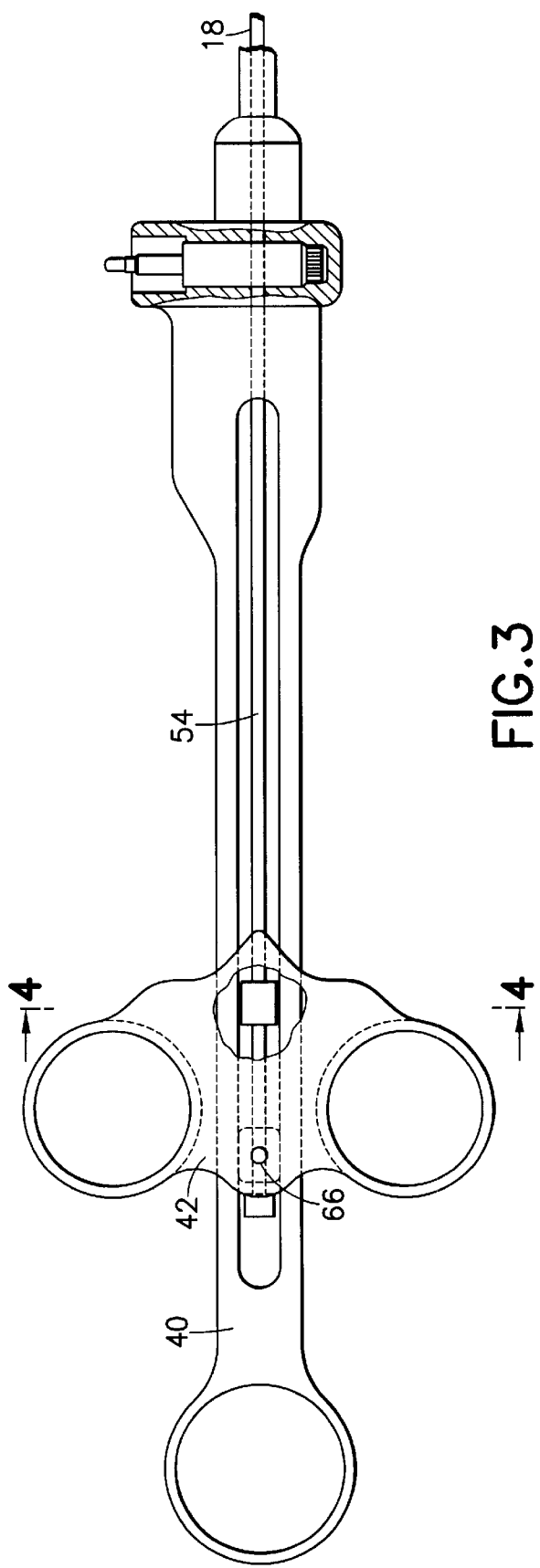
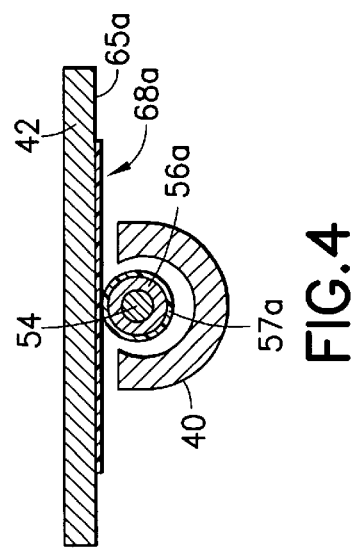
FIG.3
FIG.4

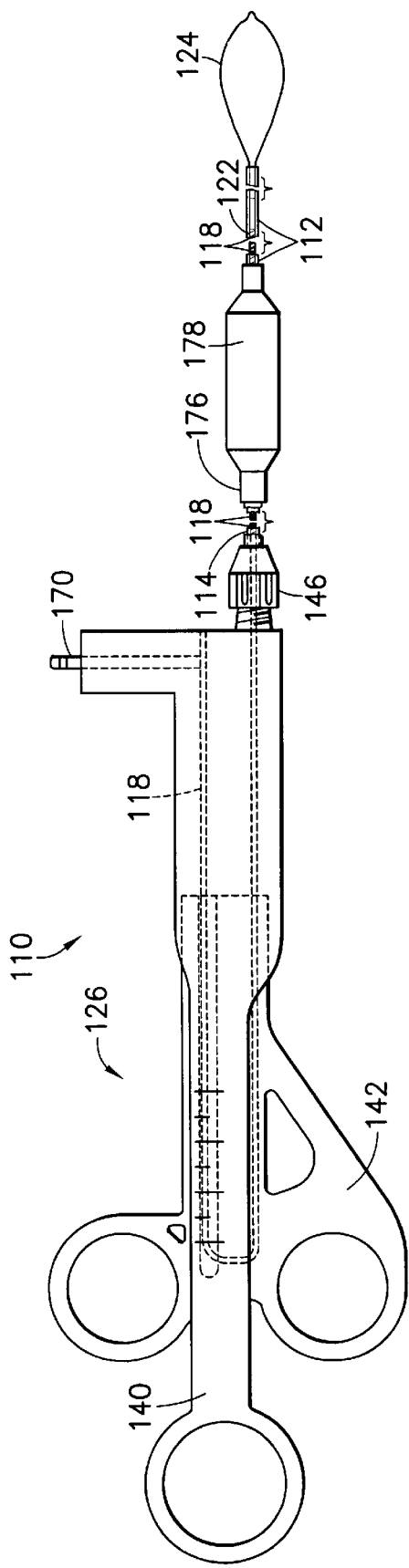
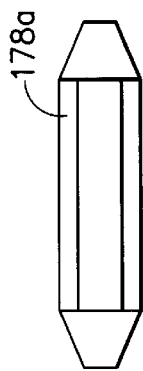
FIG. 8
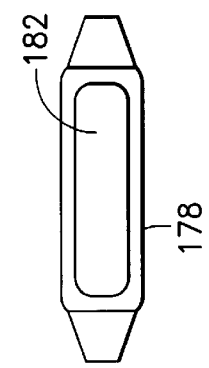
FIG. 7
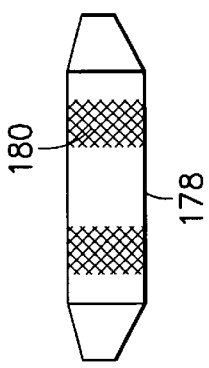
FIG. 6
FIG. 5

SURGICAL INSTRUMENT WITH ROTATABLE SHAFT

The application is a continuation-in-part of U.S. Ser. Nos. 09/143,751 and 09/143,984, both filed on Aug. 31, 1998 and both of which are continuation-in-part applications of U.S. Ser. No. 09/060,969 filed Apr. 15, 1998, a continuation-in-part of U.S. Ser. No. 09/087,476 filed on May 29, 1998, a continuation-in-part of U.S. Ser. No. 09/044,203 filed on Mar. 17, 1998, a continuation-in-part of U.S. Ser. No. 08/843,405 filed May 2, 1997, a continuation-in-part of U.S. Ser. No. 08/963,686 filed Nov. 4, 1997, and a continuation-in-part of PCT/US97/18057 filed Oct. 7, 1997 and claiming priority from U.S. Ser. Nos. 08/730,489 filed Oct. 11, 1996, 08/856,571 filed May 15, 1997, and 08/554,336 filed Nov. 6, 1995, all of which are hereby incorporated by reference herein in their entireties.

BACKGROUND OF THE INVENTION

1. Field of the Invention

This invention relates broadly to surgical instruments. More particularly, this invention relates to a surgical snare instrument for excising polyps.

2. State of the Art

Surgical snare instruments are used for the endoscopic removal of hypertrophic tissue growths within a body cavity, and particularly within the colon. Snare instruments generally include an elongated tubular member, such as a catheter sheath, a shaft extending through the tubular member, and an elastic wire (e.g., stainless steel or Nitinol) forming a loop movable distally and proximally within the tubular member. The loop can be opened by moving the loop beyond the distal end of the tubular member and closed by retraction into the tubular member, each effected by movement of the shaft relative to the sheath. A handle is provided at the proximal end of the instrument to facilitate this movement.

With the loop of the snare instrument in a retracted position, the distal end of the instrument is inserted through an endoscope into the colon and moved adjacent a polyp or other tissue growth which is identified for removal. The handle of the instrument is then operated to expand the loop of the snare and an attempt is made to maneuver the loop to surround the polyp. If successful, the loop is then constricted about the polyp to excise it. Additionally, the snare instrument may be provided with cautery capability in order to limit bleeding and thereby enhance the polyp removal procedure.

It will be appreciated that manipulation of the loop of the snare instrument about the polyp is a difficult, and sometimes unattainable, task. The expanded snare loop often lies in a plane which is not conducive for maneuvering about the polyp. Therefore, the desired polyp retrieval often cannot be achieved with the snare instrument and a more invasive procedure may be required to remove the hypertrophic growth. None of the prior art provides a means for rotating the snare loop into another plane of orientation to facilitate growth entrapment. Furthermore, none of the prior art even addresses this need.

It is however known in the laparoscopic art to provide means for permitting end effectors of laparoscopic instruments to be rotated relative to the tubular sheath of the instrument. However, laparoscopic instruments typically are relatively short devices and utilize a relatively stiff control rod which effectively translates rotational movement from the proximal end to the distal end of the instrument. As such, laparoscopic instruments are not subject to the difficulties presented by the need to rotate flexible shafts.

In addition, U.S. Pat. No. 5,788,710 to Bates et al. discloses an endoscopic mechanical lithotripsy instrument for crushing calculi in the gastrointestinal tract. The instrument includes a distal basket assembly and purports to permit controlled rotation of the basket assembly via proximal manipulation. The instrument includes a relatively long tubular sheath (typically up to eight feet in mechanical lithotripsy instruments), a 4×7 stainless steel flexible cable shaft of similar length extending through the sheath, a handle at the proximal end of the device for moving the shaft relative to the sheath and for applying torsional force to the proximal end of the shaft, and the surgical basket assembly at the distal end of the sheath for entrapping and crushing a calculus. While Bates et al. states that rotating the proximal end of the shaft, via the handle, causes a like amount of rotation of the basket assembly about the longitudinal axis of the instrument, it has been found that the described cable shaft does not function as described to provide the controlled rotation. The stainless steel cable shaft is incapable of translating the proximal torque into controllable movement of the distal basket. Rather, when rotational movement is applied to the proximal end of the shaft, the proximal end of the shaft twists without imparting any movement to the distal end of the instrument until sufficient torsional force is stored in the shaft to cause the basket assembly to rotate rapidly and uncontrollably to release the stored force.

SUMMARY OF THE INVENTION

It is therefore an object of the invention to provide a surgical instrument having a relatively long flexible shaft, wherein rotation of the proximal end of the shaft is translated into controlled rotation of the distal end of the shaft.

It is another object of the invention to provide a surgical snare instrument having a relatively long flexible shaft, wherein rotation of the proximal end of the shaft is translated into controlled rotation of the distal end of the shaft thereby permitting a snare loop at the end of the shaft to be rotatably oriented.

It is a further object of the invention to provide a surgical snare instrument which includes a proximal handle which permits rotation of a proximal end of the shaft, and a shaft adapted to provide rotation of the distal end of the instrument in a one to one ratio with rotation of the proximal end.

It is an additional object of the invention to provide a surgical snare instrument having a handle which is adapted to rotate the proximal end of the shaft and a shaft which translates the proximal rotation into controlled rotation of the distal end of the shaft, and which further includes cautery capability.

In accord with these objects, which will be discussed in detail below, a surgical snare instrument is provided. The snare instrument includes an elongated tubular sheath having proximal and distal ends, a flexible torqueable shaft having proximal and distal ends extending through and axially movable relative to the sheath, a snare loop at the distal end of the shaft, and a handle assembly coupled to the proximal ends of the sheath and shaft for moving the shaft axially and rotatably relative to the sheath so that the snare loop, when axially moved beyond the distal end of the sheath, is rotatable relative to the distal end of the sheath.

The flexible shaft is preferably a multifilament twisted and drawn cable. The filaments of the multifilament twisted and drawn cable are preferably either stainless steel, nickel-titanium alloy, or a combination of the two. Such a shaft provides the high torqueability necessary for controlled rotation of the snare loop. In addition, the shaft is capable of carrying a cautery current.

In a first preferred embodiment of the handle, the handle assembly includes a stationary member and a movable member axially and rotatably movable relative to the stationary member. The stationary member has a proximal thumb ring, a distal coupling to which the sheath is coupled, and a central longitudinal slot in communication with the sheath. The movable member includes two finger rings (fixed relative to each other) for facilitating relative axial and rotational movement of the movable member. A relatively rigid drive shaft provided with a pinion is coupled to the proximal end of the flexible shaft and extends through the longitudinal slot of the stationary member. A mounting member includes a bore in which the proximal end of the drive shaft is received and in which the drive shaft is permitted to rotate. The movable member is coupled to the mounting member so that the movable member may be pivoted about a line transverse to the drive shaft. The movable member is provided with a plurality of teeth arranged along a radial arc forming a rack which engages the pinion of the drive shaft. As such, axial movement of the movable member relative to the stationary member causes the loop at the distal end of the flexible shaft to be moved axially in and out of the tubular sheath. In addition, pivoting the movable member relative to the mounting member causes the rack to rotate the pinion and, consequently, the drive shaft and flexible shaft coupled thereto. Furthermore, the stationary member may be provided with a cautery assembly permitting a cautery current to be applied to the flexible shaft and the snare loop.

According to a second embodiment of the invention, the handle assembly includes a stationary member and a slidable member axially movable relative to the stationary member. The flexible shaft is coupled to the slidable member in a manner which does not permit rotation of the slidable member relative to the flexible shaft. The proximal end of the sheath is coupled to the stationary member so as to permit the stationary member and the flexible shaft to be rotated relative to the sheath. A stabilizing member may be fixedly coupled over a proximal portion of the sheath to facilitate relative rotational movement of the flexible shaft and sheath. As such, the slidable member may be moved relative to the stationary member to deploy and retract the snare loop, and the entire handle may be rotated relative to the sheath, facilitated by use of the stabilizing member, to rotate the snare loop relative to the distal end of the sheath. In addition, the handle may be adapted to provide cautery capability to the snare loop.

According to a third embodiment of the invention, the handle assembly includes a first member having a thumb loop and a longitudinal slot, and a second member slidably positioned within the slot and coupled to the proximal end of the flexible shaft. A third member having a longitudinal bore and a cautery plug assembly is provided relatively distal the first member. The third member is rotatably coupled to the first member so that the slot and bore are axially aligned. In addition, the proximal end of the sheath is coupled to the distal end of the third member in alignment with the bore. Axial movement of the second member relative to the first member causes axial movement of the flexible shaft relative to the sheath and resultant deployment and retraction of the snare loop. Rotational movement of the first and second members relative to the third member causes rotational movement of the snare loop relative to the sheath.

Additional objects and advantages of the invention will become apparent to those skilled in the art upon reference to the detailed description taken in conjunction with the provided figures.

BRIEF DESCRIPTION OF THE DRAWINGS

FIG. 1 is partial broken side elevation of a first embodiment of a snare instrument according to the invention;

FIG. 2 is a section view taken across line 2—2 in FIG. 1;

FIG. 3 is a partial broken side elevation of an alternate first embodiment of a snare instrument according to the invention;

FIG. 4 is a section view taken across line 4—4 in FIG. 3;

FIG. 5 is a broken side elevation of a second embodiment of a snare instrument according to the invention;

FIGS. 6, 7, and 8 are side views of alternative embodiments of a stabilizing member according to the second embodiment of the invention;

DETAILED DESCRIPTION OF THE PREFERRED EMBODIMENTS

Figure 9:
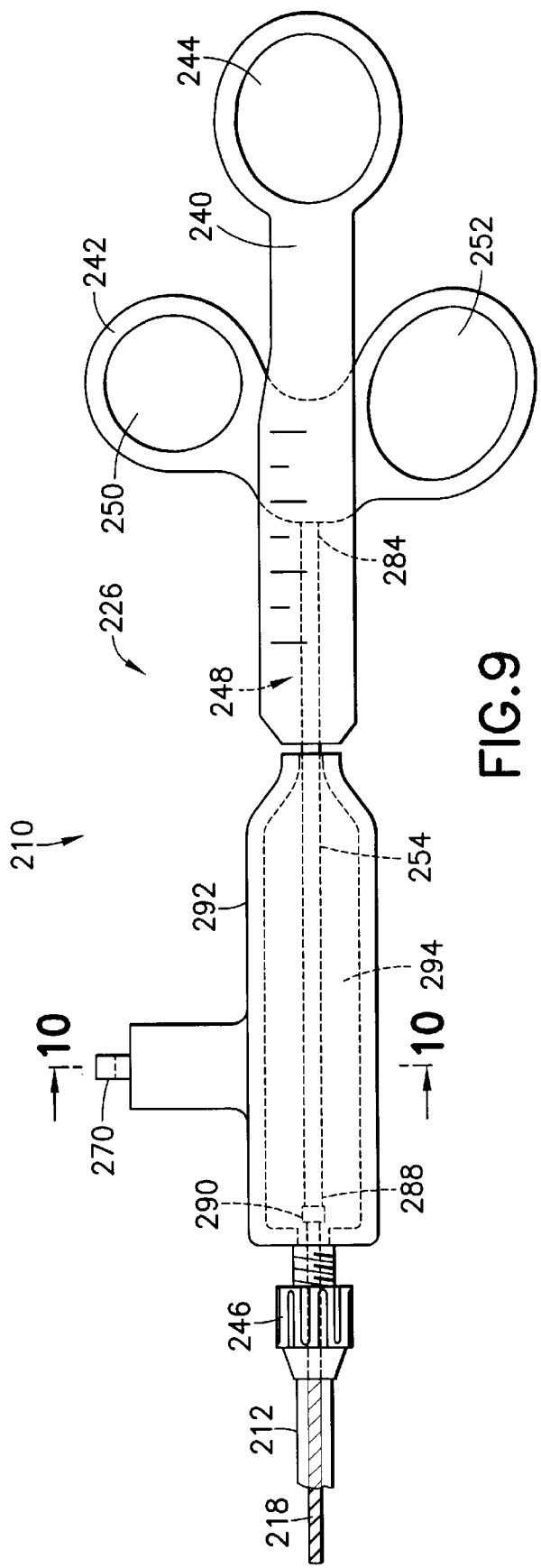
FIG. 9 is a broken side elevation of a third embodiment of a snare instrument according to the invention.

Turning now to FIG. 1, a surgical snare instrument according to the invention is shown. The snare instrument 10 includes an elongated flexible tubular sheath 12 having a proximal end 14 and a distal end 16, a flexible torqueable shaft 18 having a proximal end 20 and a distal end 22 extending through and axially movable relative to the sheath 12, a snare loop 24 coupled to the distal end 22 of shaft 18, preferably adjacent the distal end 16 of the sheath 12, and a handle assembly 26 for moving the shaft 18 relative to the sheath 12 and for rotating the shaft 18 relative to the sheath 12 so that the snare loop 24, when extended beyond the distal end 16 of the sheath, is rotatable relative to the distal end of the sheath.

The shaft 18 is preferably a multifilament twisted and drawn cable. The filaments of the multifilament twisted and drawn cable are preferably either stainless steel, nickel-titanium alloy, or a combination of the two. Such a shaft provides the high torqueability necessary for controlled rotation of the snare loop. In fact, the multifilament twisted and drawn cable shaft of the invention actually provides a one to one rotation transmission between the proximal and distal ends even when the shaft is threaded through a long and tortuous catheter path. The construction of multifilament twisted and drawn cables for a medical device is generally disclosed in previously incorporated U.S. Ser. No. 08/856,571, and multifilament twisted and drawn cables comprised at least in part of nickel-titanium alloy are particularly disclosed in previously incorporated U.S. Ser. Nos. 09/044,203, 09/060,969, and 09/087,476.

The snare loop 24 is preferably formed from a length 30 of multifilament twisted and drawn cable, or another resilient cable or wire, having first and second ends 32, 34 attached at 38 to the distal end 22 of the shaft 18, for example, by welding, soldering or crimping, and having its loop portion preferably cold formed to a desired expanded shape. Alternatively, the shaft may be formed from a resilient cable or wire which has first and second ends proximally twined and an untwined looped central portion which is preferably cold-formed to the desired shape.

The handle assembly 26 includes a stationary member 40 and a movable member 42 axially and rotatably movable relative to the stationary member 40, as described below. The stationary member 40 has a proximal thumb ring 44, a distal threaded coupling 45 to which the sheath 12 is coupled with a ferrule nut 46, and a central longitudinal slot 48 in communication with the sheath 12. The movable member 42 includes two finger rings 50, 52 for facilitating relative axial and rotational movement of the movable member 42. The finger rings 50 and 52 are preferably fixed relative to each other.

A relatively rigid drive shaft 54 provided with a pinion 56 is coupled at 57, e.g, by welding, soldering, or crimping, to the proximal end 20 of the flexible shaft 18 and extends through the longitudinal slot 48 of the stationary member 40. A mounting member 58 includes a longitudinal bore (not shown) in which the proximal end of the drive shaft 54 is received and in which the drive shaft is permitted to rotate. Bearings 60, 62 maintain the drive shaft 54 in a centered position within the slot 48. The mounting member 58 also includes a radial bore 64 at which the movable member 42 is coupled to the mounting member by a pin 66 such that the movable member may be pivoted about the pin 66 which is located on a line transverse to the drive shaft 54. Referring to FIGS. 1 and 2, the movable member 42 is provided with a plurality of teeth 68 arranged along a radial arc to form a rack which engages the pinion 56 of the drive shaft 54.

Axial movement of the movable member 42 relative to the stationary member 40 (by axial movement of a physician's thumb in thumb ring 44 relative to movement of the physician's fingers in finger rings 50, 52) causes the drive shaft 54 and hence the flexible shaft 18 to move axially, and therefore cause the snare loop 24 at the distal end 22 of the flexible shaft 18 to be moved axially in and out of the tubular sheath 12. In addition, pivotal movement of the movable member 42 about the pin 66 (by pulling one finger in finger rings 50, 52 and pushing the other finger in finger rings 50, 52) causes the teeth 68 of the rack to rotate the pinion 56 and, consequently, the drive shaft 54, the flexible shaft 18, and the snare loop 24 coupled thereto. Importantly, the use of the multifilament twisted and drawn cable as the flexible shaft 18 enables this rotation to be controlled. Preferably, for each degree of rotation at the proximal end of the shaft, the shaft 18 transfers substantially one degree of rotation to the distal end of the shaft and the snare loop; that is, proximal rotation causes distal rotation in substantially a one to one ratio.

Turning now to FIGS. 3 and 4, an alternative arrangement for rotating the drive shaft 54 with the handle assembly 26 is shown. The movable member 42 is pivotably coupled to the drive shaft 54 and slidable relative to the stationary member 40 as described above. The underside 65a of the movable member 42 is provided with a high friction surface 66a. A friction roller 56a is coupled over the drive shaft 54. At least a portion of the circumference of the friction roller 56a is provided with a high friction surface 57a. When the movable member 42 is pivoted about pin 66, movement of the high friction surface 65a over the friction roller 56a causes rotation of the friction roller 56a and, consequently, the drive shaft 54, the flexible shaft 18, and the snare loop coupled thereto.

Turning back to FIG. 1, the stationary member 40 is preferably provided with a cautery plug 70 which is coupled to the rotatable drive shaft 54. One manner of coupling the cautery plug to the axially and rotationally movable drive shaft is via an electrically conductive brush 72 having bristles 74 in contact with the drive shaft 54.

A reinforcement sleeve 76 is preferably provided over the proximal end 14 of the sheath 12 to prevent damage to the sheath from movement of the drive shaft 54 which may extend partly into the sheath.

It will be appreciated that the snare instrument of the invention permits controlled orientation of the snare loop in a manner previously not possible. As such, hypertrophic growth excision is facilitated.

Turning now to FIG. 5, a second embodiment of the snare instrument 110 of the invention (substantially similar to the first, with like parts having numbers incremented by 100) is shown. The snare instrument 110 includes a flexible tubular sheath 112, a torqueable shaft 118 (preferably comprised of a multifilament twisted and drawn cable) extending through the sheath and having at its distal end 122 a snare loop 124 coupled thereto or formed thereat. A handle assembly 126 is provided for moving the shaft 118 axially and rotationally relative to the sheath 112. The handle assembly 126 is substantially of the type provided with the polypectomy snare sold under the SENSATION trademark by the Microvasive Division of Boston Scientific Corporation, Watertown, Mass.

Generally, the handle assembly 126 includes a stationary member 140 and a slidable member 142 axially movable relative to the stationary member. The flexible shaft 118 is coupled to the slidable member 142 in a manner which does not permit rotation of the slidable member 142 relative to the flexible shaft 118. Unlike the prior art SENSATION device, the proximal end 114 of the sheath 112 is rotatably coupled to the distal end of the stationary member 140, e.g, via a ferrule nut 146, so as to permit the handle assembly 126 and the flexible shaft 118 to be rotated relative to sheath 112. For example, the proximal end 114 of the sheath 112 may be flared and held between the distal end of the stationary member 140 and the ferrule nut 146. A reinforcement sleeve 176 is preferably fit over the proximal end of the sheath 112, and a generally cylindrical stabilizing member 178 may be fixedly coupled over the reinforcement sleeve 176 to facilitate manually holding the sleeve 176 and sheath 112 stationary while the handle assembly 126 is rotated relative thereto.

Referring to FIGS. 6 and 7, the stabilizing member 178, in addition to being generally cylindrical, may be provided with knurls 180 or provided with flat portions 182. Referring to FIG. 8, alternatively, the stabilizing member 178a may be provided with a polygonal cross-sectional shape, e.g, hexagonal. Each of the above designs enhances finger traction on the stabilizing member 178 to facilitate movement of the handle assembly 126 relative to the sheath 112.

The slidable member 142 may be moved relative to the stationary member 140 to deploy and retract the snare loop 124 from and into the distal end of the sheath. In addition, the entire handle assembly 126 may be rotated relative to the sheath 112, facilitated by use of the stabilizing member 178, to rotate the snare loop 124 relative to the distal end of the sheath 112.

In addition, the handle assembly 126 may be adapted to provide cautery capability to the snare loop 124. A cautery pin 170 in the stationary member 140 of the handle assembly is conductively coupled to the proximal end of the flexible shaft 118. Because the handle assembly 126 rotates with the shaft 118, the connection of the cautery pin 170 to the shaft 118 may be by soldering, if desired.

Referring now to FIG. 9, a third embodiment of the snare instrument 210 of the invention (substantially similar to the first, with like parts having numbers incremented by 200) is shown. The snare instrument 210 includes a flexible tubular sheath 212, a torqueable shaft 218 extending through the sheath 212 and having at its distal end a snare loop coupled thereto or formed thereat. A handle assembly 226 is provided for moving the shaft 218 axially and rotationally relative to the sheath 212. The handle assembly 226 is generally similar to the type provided with the polypectomy snare sold under the CAPTIVATOR trademark by the Microvasive Division of Boston Scientific Corporation, Watertown, Mass. However, as will be appreciated from comparison of the CAPTIVATOR polypectomy snare and the snare instrument of the invention, the details of the handle assembly 226 differ significantly.

The handle assembly 226 includes a first member 240 having a thumb loop 244 and a longitudinal slot 248, and a second member 242 having finger loops 250, 252. The second member 242 is positioned in the slot 248 and axially movable relative to the first member 240. A relatively rigid conductive shaft or rod 254 has a proximal end 284 coupled to the second member 242 and a distal end 288 coupled at 290 to the flexible shaft 218. A third member 292 having a longitudinal bore 294 and a cautery plug 270 is provided relatively distal the first member 240. The third member 292 is rotatably coupled to the first member 240 so that the slot 248 and bore 294 are axially aligned. In addition, the proximal end of the sheath 212 is coupled to the distal end of the third member 292 with a ferrule nut 246 in alignment with the bore 294.

Figure 10:
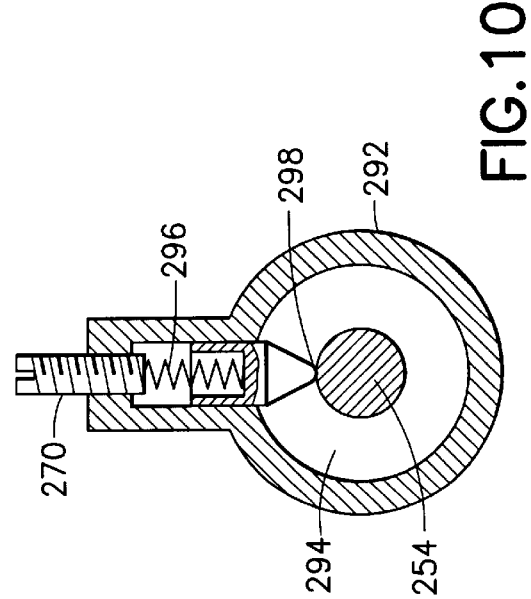
FIG. 10 is a section view taken across line 10—10 in FIG. 9.

The cautery plug 270 is coupled to the rod 254 in a manner which permits the rod to move axially and rotationally relative to the cautery plug while maintaining an electrical connection therebetween. As shown in FIG. 10, one manner of facilitating this connection is by coupling a spring 296 to the plug 270 and positioning a contact 298 between the spring 296 and the rod 254. The spring 296 forces the contact 298 against the rod 254 regardless of the axial or rotational movement of the rod.

Returning to FIG. 9, movement of the second member 242 relative to the first member 240 causes movement of the flexible shaft 218 relative to the sheath 212 and resultant deployment and retraction of the snare loop (not shown). Rotational movement of the first and second members 240, 242 relative to the third member 292 causes rotational movement of the shaft 218 and snare loop relative to the sheath 212. It will be appreciated that because the cautery plug is provided on the third member, rotation of the first and second members relative to the third member does not result in entanglement of a cautery current supply cable coupled to the cautery plug 270.

There have been described and illustrated herein several embodiments of a surgical endoscopic instrument and particularly a surgical snare instrument. While particular embodiments of the invention have been described, it is not intended that the invention be limited thereto, as it is intended that the invention be as broad in scope as the art will allow and that the specification be read likewise. Thus, while the use of a torqueable shaft has been particularly disclosed with respect to a snare instrument, it will be appreciated that other flexible shaft surgical instruments may also be provided with a torqueable shaft of the invention. For example, a similar instrument may be provided with lithotripsy basket assembly at its distal end, thereby enabling the basket to be controllably rotated. Other surgical assemblies may alternatively be provided for the instrument. In addition, while the torqueable shaft is described as being multifilament twisted and drawn cable, it will be appreciated that the shaft may be made from a multifilament twisted and swaged cable or twisted and rolled cable. Furthermore, while particular types of handle assemblies have been disclosed, it will be understood that other handle assemblies permitting axial and rotational movement of the flexible shaft relative to the sheath can also be used. Moreover, the handle of the first embodiment may be used with other surgical instruments where both axial and rotational movement of a control member relative to a tubular member is required. For example, the handle may be used in laparoscopic and endoscopic instruments, generally. In addition, while the first embodiment discloses pivotably moving the movable member relative to the drive shaft, it will be appreciated that the movable member may be transversely movable relative to the drive shaft, e.g., on a track, to cause rotation of the drive shaft. Also, in each embodiment, the movable member and stationary member may be adapted to be locked relative to each other. It will therefore be appreciated by those skilled in the art that yet other modifications could be made to the provided invention without deviating from its spirit and scope as claimed.

What is claimed is:

1. A surgical instrument, comprising:
   a) an elongated flexible tubular sheath having proximal and distal ends;
   b) a flexible shaft having proximal and distal ends extending through and axially and rotationally movable relative to said sheath, with a snare loop being provided at said distal end of said flexible shaft; and
   c) a handle assembly comprising a thumb ring and two finger rings which is adapted to move said shaft and said sheath axially and rotationally relative to each other.

2. A surgical instrument according to claim 1, wherein: said handle assembly includes means for applying a cautery current to said flexible shaft.

3. A surgical instrument according to claim 1, wherein: said handle assembly includes a first member and a second member axially movable relative to said first member, said first member being coupled to said sheath, and said second member being coupled to said flexible shaft.

4. A surgical instrument according to claim 3, further comprising:
   d) a second shaft relatively stiffer than said flexible shaft, said second shaft having a proximal end coupled to said second member and a distal end coupled to said flexible shaft.

5. A surgical instrument according to claim 4, further comprising:
   e) a relatively stiff sleeve provided over said proximal end of said sheath.

6. A surgical instrument according to claim 3, wherein: said sheath is rotatably coupled to said first member of said handle assembly.

7. A surgical instrument according to claim 6, wherein: said sheath is provided with a means for manually assisting rotation of said sheath relative to said flexible shaft.

8. A surgical instrument according to claim 1, wherein: said handle assembly includes a first member, a second member coupled to said proximal end of said flexible shaft and axially movable relative to said first member, and a third member coupled to said proximal end of said sheath, said first and second members being rotationally movable relative to said third member.

9. A surgical instrument according to claim 8, wherein: said third member has a means for applying a cautery current to said flexible shaft.

10. A surgical instrument comprising:
    a) an elongated flexible tubular sheath having proximal and distal ends;
    b) a flexible shaft having proximal and distal ends extending through and axially and rotationally movable relative to said sheath, with a snare loop being provided at said distal end of said flexible shaft; and c) a handle assembly which is adapted to move said shaft and said sheath axially and rotationally relative to each other;

wherein:

said flexible shaft is constructed so that when said proximal end of said flexible shaft is rotated a first degree relative to said proximal end of said sheath, said snare loop at said distal end of said flexible shaft is rotated approximately said first degree relative to said distal end of said sheath.

11. The instrument of claim 10, wherein said handle assembly is adaptable for being operated single-handedly.

12. The instrument of claim 10, wherein said handle assembly is adaptable for being operated with more than one hand.

13. A surgical instrument comprising:

a) an elongated flexible tubular sheath having proximal and distal ends;

b) a flexible shaft having proximal and distal ends extending through and axially and rotationally movable relative to said sheath, with a snare loop being provided at said distal end of said flexible shaft; and c) a handle assembly which is adapted to move said shaft and said sheath axially and rotationally relative to each other;

wherein:

said flexible shaft is constructed of a resilient material having the torqueability of a multifilament twisted and drawn or twisted and swaged or twisted and rolled cable.

14. A surgical instrument according to claim 13, wherein:

said multifilament twisted and drawn or swaged cable includes at least one of a steel filament and a nickel-titanium alloy filament.

15. The instrument of claim 13, wherein said handle assembly is adaptable for being operated single-handedly.

16. The instrument of claim 13, wherein said handle assembly is adaptable for being operated with more than one hand.

17. A surgical instrument comprising:

a) an enlongated flexible tubular sheath having proximal and distal ends;

b) a flexible shaft having proximal and distal ends extending through and axially and rotationally movable relative to said sheath, with a snare loop being provided at said distal end of said flexible shaft; and c) a handle assembly which is adapted to move said shaft and said sheath axially and rotationally relative to each other;

wherein:

said handle assembly includes a first member and a second member axially relative to said first member, said second member being coupled to said sheath, and said second member being coupled to said flexible shaft; and further comprising:

d) a second shaft relatively stiffer than said flexible shaft, said second shaft having a proximal end coupled to said second member and a distal end coupled to said flexible shaft;

wherein:

said second shaft is provided with a pinion, and second member of said handle assembly is provided with a rack which engages said pinion, said second member being movable relative to said second shaft, wherein when said second member is moved relative to said second shaft, said rack causes rotation of said pinion and said flexible shaft.

18. A surgical instrument according to claim 17, wherein:

said second member is pivotably movable relative to said second shaft.

19. A surgical instrument according to claim 17, wherein:

said second member is pivotably movable relative to said second shaft.

20. A surgical instrument comprising:

a) an elongated flexible tubular sheath having proximal and distal ends;

b) a flexible shaft having proximal and distal ends extending through and axially and rotationally movable relative to said sheath, with a snare loop being provided at said distal end of said flexible shaft; and c) a handle assembly which is adapted to move said shaft and said sheath axially and rotationally relative to each other;

wherein:

said handle assembly includes a first member and a second member axially relative to said first member, said first member being coupled to said sheath, and said second member coupled to said flexible shaft; and futher comprising:

d) a second shaft relatively stiffer than said flexible shaft, said second shaft having a proximal end coupled to said second member and a distal and coupled to said flexible shaft;

wherein:

said second shaft is provided with a roller, and second member of said handle assembly is provided with a surface which frictionally engages said roller, said second member being movable relative to said second shaft, wherein when said second member is moved relative to said second shaft, movement of said surface relative to said roller causes rotation of said roller and said flexible shaft.

21. A surgical instrument, comprising:

a) an elongated flexible tubular sheath having proximal and distal ends;

b) a flexible shaft having proximal and distal ends extending through and axially movable relative to said sheath, a surgical assembly being provided at said distal end of said shaft; and c) a handle assembly for controllably moving said shaft and said sheath axially and rotationally relative to each other, wherein said flexible shaft is constructed so that when said proximal end of said flexible shaft is rotated a first degree relative to said proximal end of said sheath, said surgical assembly at said distal end of said flexible shaft is rotated approximately said first degree relative to said distal end of said sheath.

22. A surgical instrument according to claim 21, wherein:

said handle assembly includes means for applying a cautery current to said flexible shaft.

23. A surgical instrument according to claim 21, further comprising:

d) a second shaft relatively stiffer than said flexible shaft, said second shaft having a proximal end and a distal end and being provided with a pinion, said handle assembly including a first member and a second member axially movable relative to said first member, said second member being provided with a rack which engages said pinion of said second shaft and said second member being movable relative to said second shaft, said first member being coupled to said sheath, said second member being coupled to said proximal end of said second shaft, and said proximal end of said flexible shaft being coupled to said distal end of said second shaft, wherein when said second member is moved relative to said second shaft, said rack causes rotation of said pinion and said flexible shaft.

24. A surgical instrument according to claim 23, wherein:

said second member is pivotably movable relative to said second shaft.

25. The instrument of claim 21, wherein said handle assembly is adaptable for being operated single-handedly.

26. The instrument of claim 21, wherein said handle assembly is adaptable for being operated with more than one hand.

27. A surgical instrument comprising:
a) an enlongated tubular sheath having proximal and distal ends;
b) a shaft made of resilient material having the torqueability of a multifilament twisted and drawn or twisted and swaged or twisted and rolled cable having proximal and distal ends extending through and axially movable relative to said sheath, a surgical assembly being provided at said distal end of said shaft; and
c) a handle assembly coupled to said shaft and said sheath and which is adapted to move said shaft and said sheath axially relative to each other.

28. A surgical instrument according to claim 27, wherein:

said handle assembly includes means for moving said shaft and sheath rotationally relative to each other.

29. A surgical instrument according to claim 27, wherein:

said multifilament twisted and drawn or swaged cable shaft includes at least one of a stainless steel filament and a nickel-titanium alloy filament.

30. A surgical instrument according to claim 27, wherein:

said handle assembly means includes means for applying a cautery current to said flexible shaft.

31. The instrument of claim 27, wherein said handle assembly is adaptable for being operated single-handedly.

32. The instrument of claim 27, wherein said handle assembly is adaptable for being operated with more than one hand.

33. A surgical instrument, comprising:
a) an elongated tubular member having proximal and distal ends;
b) an elongated control member extending through and axially and rotationally movable relative to said tubular member, a surgical assembly being provided at said distal end of said control member and a pinion being provided at or adjacent said proximal end; and
c) a handle assembly including a first member and a second member axially movable relative to said first member, said second member being provided with a rack which engages said pinion of said control member and said second member being movable relative to said control member,
said first member being coupled to said tubular member and said second member being coupled to said proximal end of said control member,
wherein when said second member is moved relative to said control member, said rack causes rotation of said pinion and said control member.

34. A surgical instrument according to claim 33, wherein:

said second member is pivotably movable relative to said control member.

35. A surgical instrument, comprising:
a) an elongated tubular member having proximal and distal ends;
b) an elongated control member extending through and axially and rotationally movable relative to said tubular member, a surgical assembly being provided at said distal end of said control member and a roller being provided at or adjacent said proximal end of said control member; and
c) a handle assembly including a first member and a second member axially movable relative to said first member, said second member being provided with a surface which frictionally engages said roller of said control member and said second member being movable relative to said control member,
said first member being coupled to said tubular member and said second member being coupled to said proximal end of said control member,
wherein when said second member is moved relative to said control member, said surface moves relative to said roller and causes rotation of said roller and said control member.

36. A surgical instrument according to claim 35, wherein:

said second member is pivotably movable relative to said control member.

* * * * *